US012765962B2

(12) United States Patent
Mertens et al.

(10) Patent No.: US 12,765,962 B2
(45) **Date of Patent: *Oct. 20, 2026**

(54) HEAD STABILIZATION DEVICE WITH NON-UNIFORM PINS

(71) Applicant: Black Forest Medical GmbH, Freiburg Im Breisgau (DE)

(72) Inventors: Jan H. Mertens, Freiburg (DE); Matthias E. Schuele, Freiburg (DE)

(73) Assignee: Black Forest Medical GmbH, Freiburg Im Breisgau (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/827,689

(22) Filed: Sep. 7, 2024

(65) Prior Publication Data

US 2024/0423749 A1 Dec. 26, 2024

Related U.S. Application Data

(63) Continuation of application No. 16/582,167, filed on Sep. 25, 2019, now Pat. No. 12,090,000.

(60) Provisional application No. 62/736,057, filed on Sep. 25, 2018.

(51) Int. Cl.
*A61B 90/14* (2016.01)

(52) U.S. Cl.
CPC .................................... *A61B 90/14* (2016.02)

(58) Field of Classification Search
CPC ........... A47B 7/00; A61B 90/10; A61B 90/11; A61B 90/13; A61B 90/14; A61B 2090/101; A61F 5/00; A61G 13/00; A61G 13/12; A61G 15/00
See application file for complete search history.

(56) References Cited

U.S. PATENT DOCUMENTS 12,090,000 B2 * 9/2024 Mertens ................. A61B 90/14
2009/0014011 A1 * 1/2009 Edlauer .................. A61B 90/14
128/845

* cited by examiner

*Primary Examiner* — Alireza Nia
*Assistant Examiner* — Gina Mccarthy
(74) *Attorney, Agent, or Firm* — FBT Gibbons LLP

(57) ABSTRACT

A head stabilization device having the form of a skull clamp includes a first pin assembly and a second pin assembly. The pin assemblies are positioned opposite each other, and the first pin assembly has a first pin while the second pin assembly has a pair of pins. The pins used with the skull clamp are non-uniform. In this respect skull clamp can apply an equal force to a head of a patient from both sides. Additionally, the pressure at each pin location can be the same or substantially the same. This allows each of the pins to have the same or similar bone penetration when in use stabilizing the head of the patient.

12 Claims, 7 Drawing Sheets

HEAD STABILIZATION DEVICE WITH NON-UNIFORM PINS

PRIORITY

This application claims priority to U.S. Nonprovisional patent application Ser. No. 16/582,167, filed Sep. 25, 2019, entitled "HEAD STABILIZATION DEVICE WITH NON-UNIFORM PINS," the disclosure of which is incorporated by reference herein, and which claims priority to U.S. Provisional Patent Application Ser. No. 62/736,057, filed Sep. 25, 2018, entitled "HEAD STABILIZATION DEVICE WITH NON-UNIFORM PINS," the disclosure of which is incorporated by reference herein.

BACKGROUND

The devices and methods disclosed pertain to patient stabilization, and in particular head and neck stabilization using stabilization devices known as head stabilization devices which are also referred to as head fixation devices (hereinafter referred to as "HFDs" or "HFD" in singular). HFDs are sometimes used during a variety of surgical and other medical procedures, for example during head or neck surgery or testing where it would be desirable to securely hold a patient's head in a certain position. While a variety of stabilization devices have been made and used, it is believed that no one prior to the inventor(s) has made or used an invention as described herein.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements.

Figure 1:
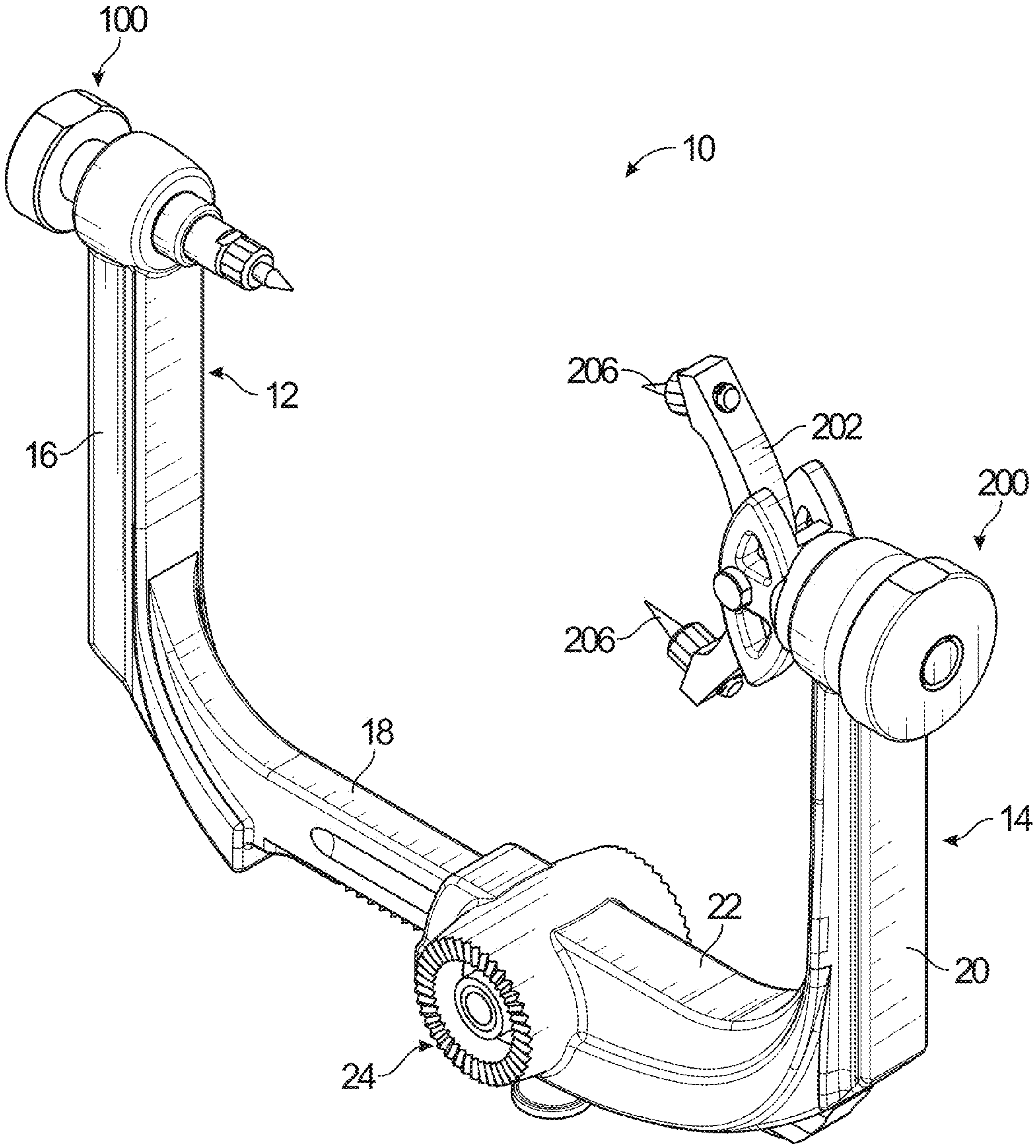
FIG. 1 depicts a perspective view of an exemplary HFD.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary HFD and Pin Configuration

FIG. 1 illustrates an exemplary HFD in the form of a skull clamp (10). While the present example illustrates the HFD as a U-shaped skull clamp, the teachings herein may be applied to other forms of HFDs as will be understood by those of ordinary skill in the art in view of the teachings herein. Skull clamp (10) comprises a first arm (12) and a second arm (14). First arm (12) is connectable with second arm (14) to form skull clamp (10) having a U-shape. First arm (12) comprises an upright portion (16) and a lateral portion (18). Similarly, second arm (14) comprises an upright portion (20) and a lateral portion (22). Skull clamp (10) is adjustable to accommodate a variety of head sizes by translating first arm (12) relative to second arm (14) or vice versa. Skull clamp (10) is further connectable to other structures, such as a positioning adapter or a base unit that is further connectable with an operating table, etc., by way of an attachment interface (24). As shown in the present example of FIG. 1, upright portion (16) of first arm (12) connects with a pin assembly (100), while upright portion (20) of second arm (14) connects with a pin assembly (200).

Figure 2:
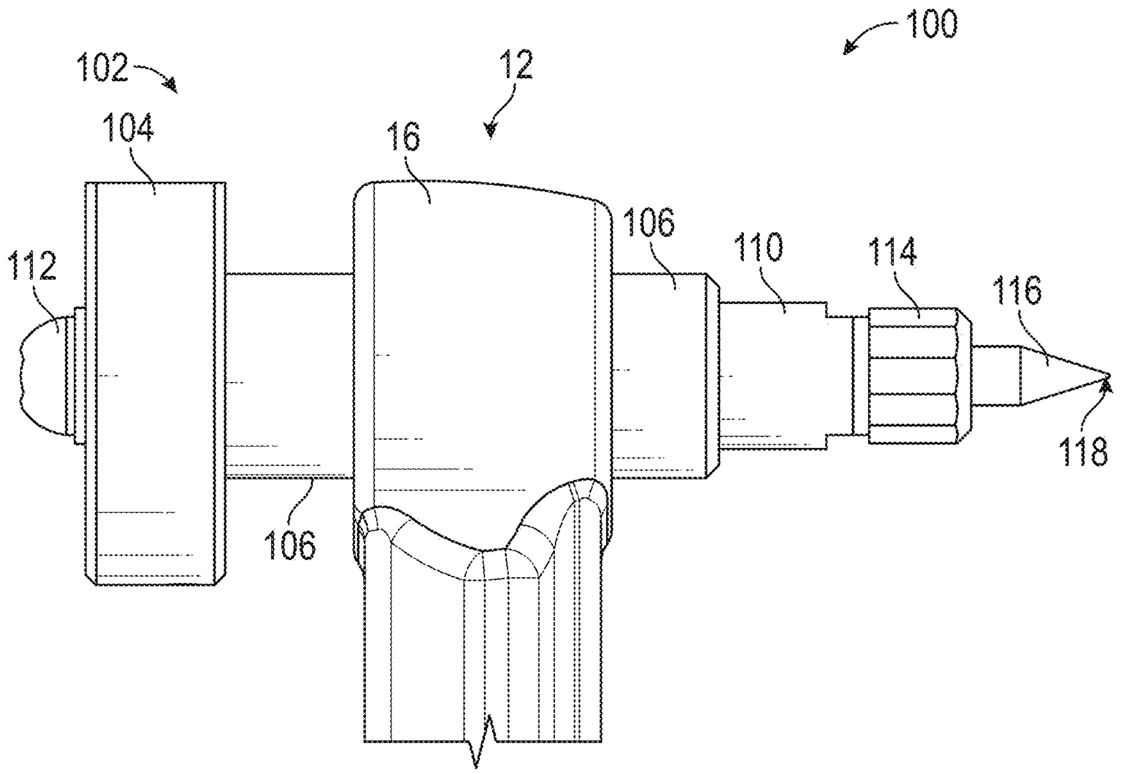
FIG. 2 depicts a partial front view of a pin holder assembly of the HFD of FIG. 1, with the pin holder assembly configured to hold a single pin.

Referring now to FIG. 2, pin assembly (100) comprises a torque screw (102) configured to adjust an amount of clamping force skull clamp (10) applies to the head of the patient. Torque screw (102) comprises a wheel (104), a sleeve (106), a spring (not shown), and an elongated member (110). Sleeve (106) has a threaded outer surface that threadably engages with a threaded bore in upright portion (16) of arm (12). Sleeve (106) has an interior space where the spring is located. At a proximal end, the spring contacts wheel (104). At a distal end, the spring contacts a flange of elongated member (110). Wheel (104) is connected with sleeve (106) such that rotation of wheel (104) causes a corresponding rotation of sleeve (106). With this configuration, as wheel (104) is rotated, wheel (104) and sleeve (106) translate relative to upright portion (16) based on the threaded engagement depending on the direction of rotation of wheel (104).

Elongated member (110) extends through a bore in wheel (104) and elongated member (110) is secured to a screw (112) at its proximal end. At its distal end, elongated member (110) retains a pin holder (114) that retains a pin (116). In use, at least a distal tip (118) of pin (116) contacts the head of the patient. When wheel (104) is rotated, such that wheel (104) and sleeve (106) translate distally towards the patient's head between pin assemblies (100, 200), the spring is compressed and thereby exerts increased force on elongated member (110) in a direction toward the patient's head.

Because elongated member (110) retains pin holder (114), which retains pin (116), this increase in force on elongated member (110) coincides with an increase in force at pin (116), which contacts the patient's head. Force applied by pin (116) to the head of the patient can be decreased by rotation of wheel (104) in the opposite direction.

Figure 3:
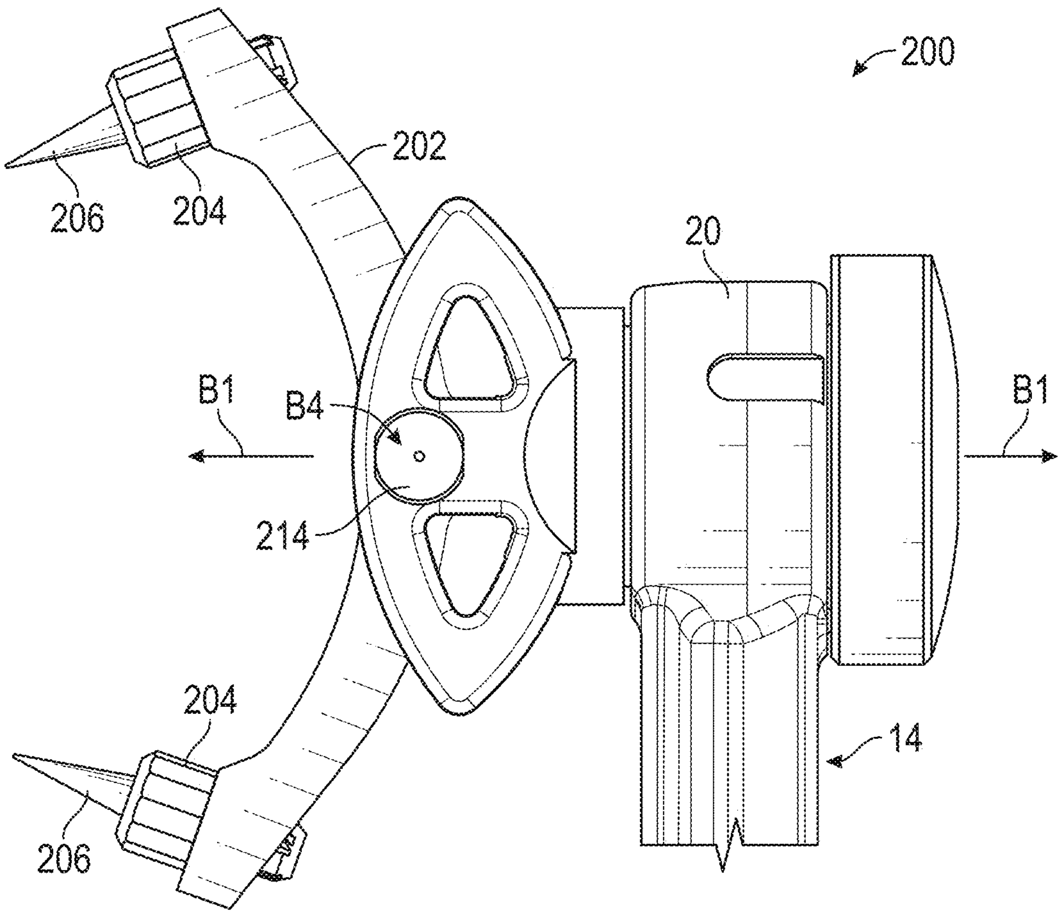
FIG. 3 depicts a partial front view of another pin holder assembly of the HFD of FIG. 1, with the pin holder assembly configured to hold a pair of pins.

Referring to FIG. 3, pin assembly (200) connects with upright portion (20) of arm (14) as shown. In the present example, this connection between pin assembly (200) and upright portion (20) is such that the lateral position of pin assembly (200) relative to upright portion (20) of arm (14), is fixed once the pivot position is set as discussed below. Pin assembly (200) comprises rocker arm (202), which retains pin holders (204), which in turn retain pins (206) configured to contact the head of the patient. Rocker arm (202) is rotatably adjustable about an axis B1 extending through a bore in upright portion (20). This rotation can be selectively controlled such that the rotatable position of rocker arm (202) can be locked in position or unlocked for adjustment. In view of the teachings herein, various ways to configure pin assembly (200) to provide locking and unlocking states for rotational adjustment will be apparent to those of ordinary skill in the art. Pin assembly (200) is also configured such that rocker arm (202) is pivotably adjustable about an axis B4 defined longitudinally by pin (214). Regardless of the rotational or pivotal adjustments, the force applied to the head of the patient via torque screw (102) of pin assembly (100) as described above, causes force to also be applied to the head of the patient from pin assembly (200) and its pins (206) that are configured to contact the head of the patient.

With the configuration described above for skull clamp (10), the head of a patient can be stabilized. By way of example only, and not limitation, in a stabilization procedure for an adult head, the force applied by pin assembly (100) can be between about 270 newtons and about 360 newtons. However, the precise amount of force used should be gauged according to a given surgeon's needs taking into consideration such things as the procedure type, the patient's bone structure and condition, etc. In some examples, the precise amount of force used may be an amount such that pin (116) and pins (206) anchor in the bone of the skull, but without penetrating the entire way through the bone. Again, the example force range provided above, as well as anywhere else, is merely exemplary and should not be interpreted as limits or limiting in any fashion. Accordingly, it should be understood that in some other examples the stabilization force used can be greater or less than the range presented above of between about 270 newtons and 360 newtons.

Figure 6:
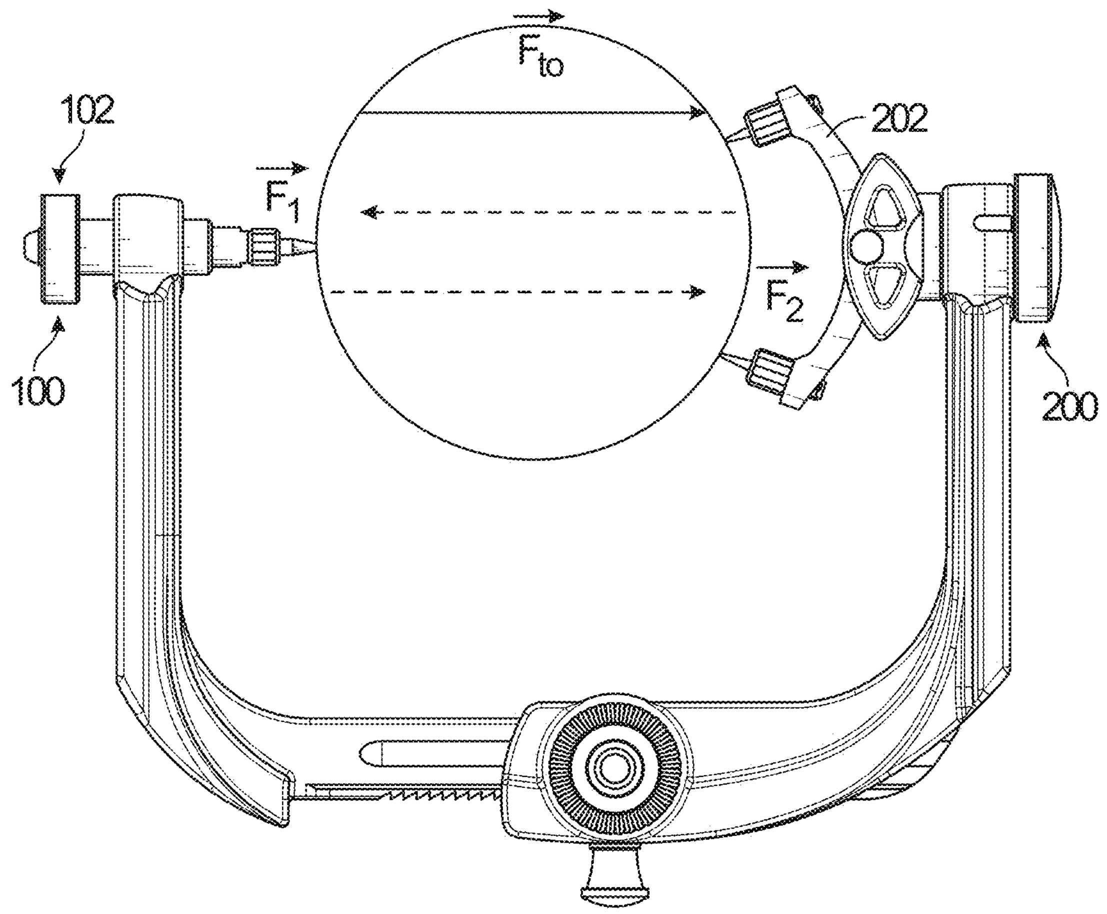
FIG. 6 depicts an exemplary HFD including an overlay of an exemplary force distribution.

Referring to FIG. 6, torque screw (102) is configured in some versions with a gage or scale that indicates the total force applied, which denoted $\vec{F}_{to}$. In an example where 360 newtons of force is applied as indicated by the scale on torque screw (102), this force is applied to both sides by pin assemblies (100, 200) as shown as $\vec{F}_1$ for the force applied by pin assembly (100), and $\vec{F}_2$ for the force applied by pin assembly (200). In an ideal setup with a perfectly round patient head, and with one skull pin on each side where the skull pins have a common longitudinal axis, $\vec{F}_1$ and $\vec{F}_2$ would each be 360 newtons. In this manner equal and opposite forces would be applied to the sides of the head of the patient. In 3-pin configurations using single pin (116) with pin assembly (100) and a pair of pins (206) with rocker arm (202) with pin assembly (200), the force distribution differs because the force applied by pair of pins (206) is divided between each pin (206) of the pair. Accordingly, in a simplified example the 360 newtons of force for $\vec{F}_2$ is divided equally between each pin (206) of the pair, such that each pin (206) applies 180 newtons of force when single pin (116) applies 360 newtons of force as indicated on the scale or gage of torque screw (102). In this example, the force applied on each side of the head of the patient is equal at 360 newtons.

The force applied to the head of the patient is an important variable in terms of the ultimate pressure applied at the head of the patient where the pins contact the head. Pressure is directly related to the applied force by the relationship that pressure P equals force F divided by area A as shown in Equation 1.

$$P = F/A \qquad \text{Equation 1}$$

In looking at skull clamp (10), the pressure at the side with pin assembly (100) would be calculated as the force $\vec{F}_1$ divided by the area. In this case, the area on the side with pin assembly (100), area $A_1$, is equal to the contact area provided by pin (116) with the head of the patient. The pressure at the side with pin assembly (200) could be calculated similarly as the force $\vec{F}_2$ divided by the area. On the 2-pin side, the force $\vec{F}_2$ is split between the two pins (206) as mentioned above. Furthermore, each pin (206) has an associated area $A_2$. So, the pressure on the 2-pin side where each pin (206) contacts the head of the patient equals half of the force $\vec{F}_2$ divided by the contact area $A_2$ provided by pin (206).

Figure 7:
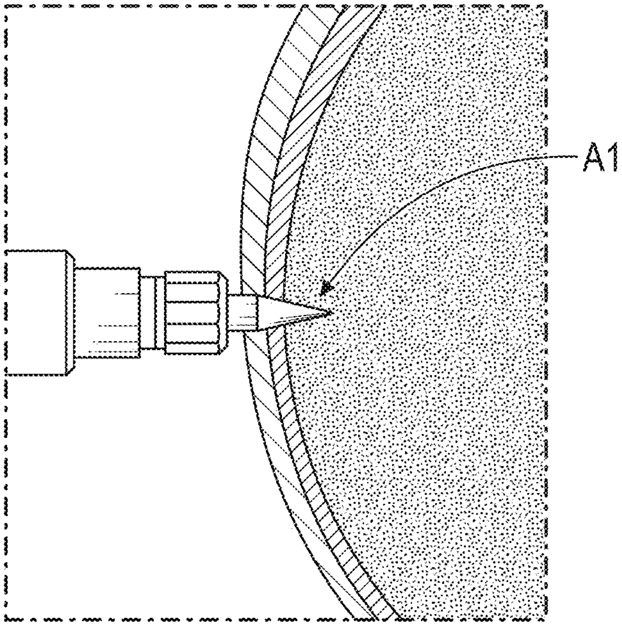
FIG. 7 depicts an imaging output showing pin penetration into a skull on the single pin side of an HFD.
Figure 8:
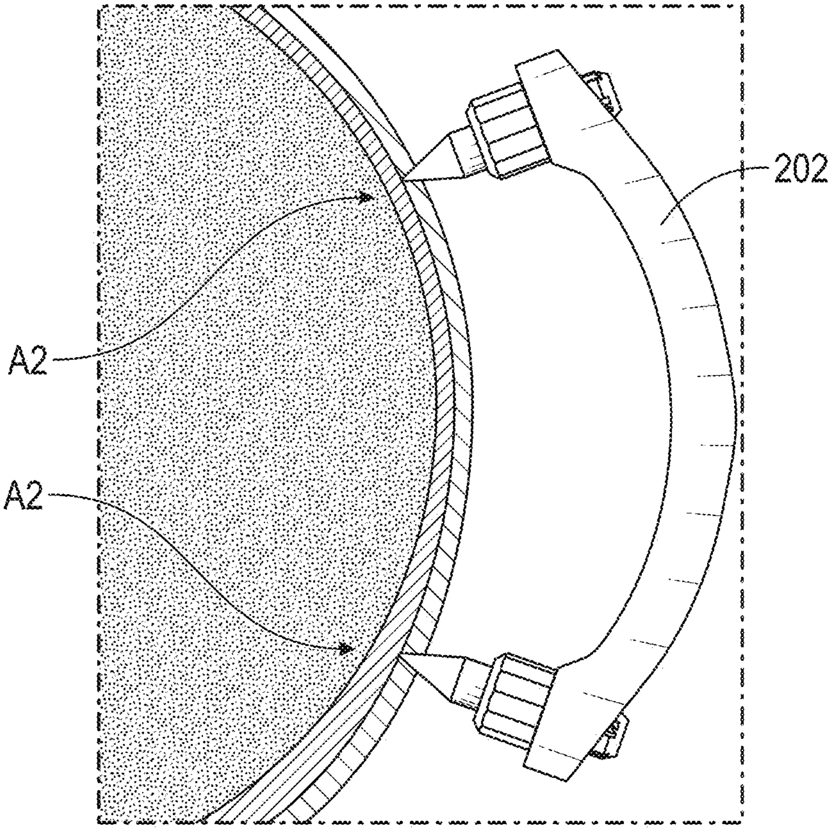
FIG. 8 depicts an imaging output showing pin penetration into a skull on the 2-pin side of an HFD.

With skull clamp configurations using a 3-pin setup where one pin assembly has a single pin and the other pin assembly has a pair of pins, using the same configuration for each pin provides that the contact area where each pin contacts the head of the patient will be the same; thus $A_1=A_2$. However, because the force $\vec{F}_2$ on the 2-pin side is split between two pins, the pressure where each pin on the 2-pin side contacts the head will be lower compared to the pressure where the single pin on the 1-pin side contacts the head. This difference in pressure can lead to different penetration depths of the pins in the skull bone as illustrated in the example of FIGS. 7 and 8 that show a CT scan of a skull clamp using uniform pin configurations for all pin locations. As seen in FIG. 7, the pin on the single pin side has penetrated too deep, breaching the skull bone. As seen in FIG. 8, the pair of pins on the 2-pin side hardly penetrate the skull bone. This pressure imbalance and its impact on skull bone penetration by the pins can compromise the rigidity or integrity of the patient's head stabilization.

Returning to skull clamp (10) with pin assemblies (100, 200) and pin (116) and pins (206), the present illustrated example of FIGS. 1-5 uses pins having differing configurations to achieve uniform or more uniform pressure at each location where one of pins (116, 206) contacts the patient's head for stabilization. For instance, in some versions it is desirable to configure skull clamp (10) such that in use, each pin (206) of pin assembly (200) generates a pressure that equals the pressure generated by single pin (116) of pin assembly (100). In the illustrated version described further below, this is achieved by using pins having different pin angles thereby altering the contact areas to influence the pressure according to the equations above. In some other versions, it can be desirable to configure skull clamp (10)

such that in use, the pin of pin assembly (100) generates a pressure that equals the pressure generated by each pin (206) of pin assembly (200).

In one example, pin assembly (100) has single pin (116) with a contact area $A_1$. Furthermore, in the present example the contact area of each pin (206) used on the 2-pin side is one-half of the contact area $A_1$ on the single pin side. Knowing, as explained above, that force $\vec{F}_2$=force $\vec{F}_1$, and that force $\vec{F}_2$ on the 2-pin side is split between two pins (206), the pressure at each of pins (206) can be represented as shown in Equation 2 below.

$$\text{Pressure at Each Pin (206)} = \left(\text{Force } \vec{F}_1/2\right)/\left(A_1/2\right) \qquad \text{Equation 2}$$

Equation 2 can be simplified to Equation 3 below, which is the same equation for calculating the pressure at pin (116).

$$\text{Pressure at Pin (116)} = \text{Force } \vec{F}_1/A_1 \qquad \text{Equation 3}$$

Thus, by reducing the contact area for pins (206) on the 2-pin side, the pressure at pins (206) is increased to match the pressure at pin (116) on the single pin side. This uniform pressure profile or distribution provides for uniform bone penetration at each location where pins (116, 206) contact the head of the patient, which in turn promotes a more rigid and secure stabilization. This also provides the ability to avoid excessive pressure use on the single pin side when trying to achieve acceptable bone penetration on the 2-pin side, thereby reducing trauma to the patient. Moreover, the uniform pressure distribution mentioned above is achieved by maintaining the same force applied to each side of the head of the patient.

Figure 4:
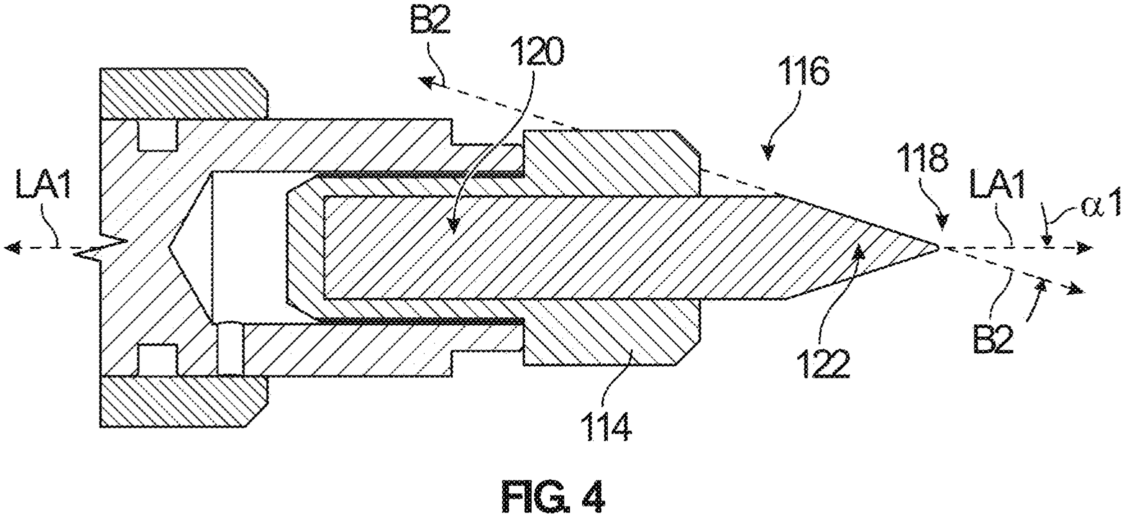
FIG. 4 depicts an enlarged cross section view of a portion of the pin holder assembly of FIG. 2.

Referring now to FIG. 4, pin (116) is shown in cross section, and defines a longitudinal axis LA1 extending through pin (116). Furthermore, pin (116) comprises a body portion (120) and a tapered portion (122). Pin (116) further defines an axis B2, which extends from distal tip (118) proximally along pin (116). The intersection of longitudinal axis LA1 and axis B2 define a pin angle α1.

Figure 5:
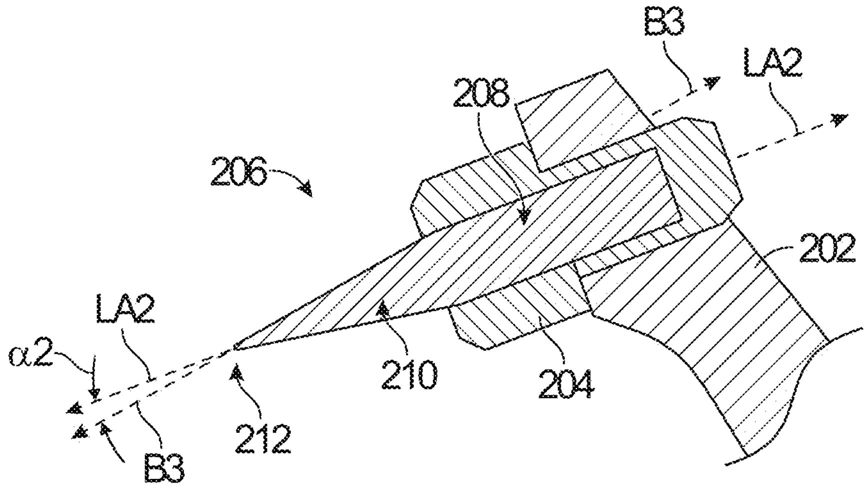
FIG. 5 depicts an enlarged cross section view of a portion of the pin holder assembly of FIG. 3.

Referring now to FIG. 5, pin (206) is shown in cross section, and defines a longitudinal axis LA2 extending through pin (206). Furthermore, pin (206) comprises a body portion (208) and a tapered portion (210). Pin (206) further defines an axis B3, which extends from a distal tip (212) proximally along pin (206). The intersection of longitudinal axis LA2 and axis B3 define a pin angle α2.

With the configuration for skull clamp (10) having a single pin (116) on one side and a pair of pins (206) on the opposite side, as shown in FIGS. 4 and 5, the pin angles differ. That is, pin (116) has a pin angle of α1, and pins (206) each have a pin angle of α2, and pin angle α1 does not equal pin angle α2. In one version of skull clamp (10), pins (206) have a pin angle α2 that is smaller than the pin angle α1 of pin (116). In some examples, the first pin angle and the second pin angle are each within the range of about 3 degrees to about 45 degrees. In some other versions this range can be about 3 degrees to about 23 degrees. In some versions of skull clamp (10), the pin angle α2 of pins (206) on the 2-pin side is greater than or equal to about 1 degree smaller than the pin angle α1 of pin (116) on the single pin side. Still in other examples of skull clamp (10), the difference in pin angle α1, α2 of pins (206) and pin (116) can be larger or smaller than 1 degree. Also, the about 1 degree difference stated in the above example is non-limiting and merely one example of a difference in pin angle α1, α2 of pins (206) and pin (116). For instance, in some versions of skull clamp (10) the pin angle α2 of pins (206) on the 2-pin side is greater than or equal to about 5 degrees smaller than the pin angle α1 of pin (116) on the single pin side. In another example, the difference in pin angle α1, α2 of pins (206) and pin (116) is such that the pin angle α2 of pins (206) is about half of the pin angle α1 of pin (116). In another version of skull clamp (10), the pin angle α1 of pin (116) and the pin angle α2 of pins (206) are each within the range of about 3 degrees to about 45 degrees with the difference between the pin angle α1 and the pin angle α2 is at least about 1 degree. In another version of skull clamp (10), the pin angle α1 of pin (116) and the pin angle α2 of pins (206) are each within the range of about 3 degrees to about 23 degrees with the difference between the pin angle α1 and the pin angle α2 is at least about 1 degree. Still yet, in another version of skull clamp (10), the pin angle α2 of pins (206) on the 2-pin side is between about 1 degree and about 5 degrees smaller than the pin angle α1 of pin (116) on the single pin side.

With the smaller pin angle α2, the contact area for pin (206) is less and therefore the force applied to and through pins (206) is applied over a smaller contact area which in turn increases the pressure. For example, with the conical shape of pins (116, 206), the contact area or surface area can be represented by Equation 4 below, where A=surface area; r=radius of the cone; and h=height of the cone.

$$A = \pi r\left(r + \sqrt{\left(h^2 + r^2\right)}\right) \qquad \text{Equation 4}$$

As the pin angle decreases, the radius decreases and thus the surface area decreases. Conversely, with larger pin angles, the radius is greater and thus the surface area is greater. As shown above, these surface areas correlate with the contact area of the pins and this directly impacts pressure applied by the pins to the head of the patient.

Another way area or contact area can be assessed is by considering the circular area of the pin in cross section at a given penetration depth relative to the skull bone. In some versions of skull clamp (10), this circular area of pins (206) on the 2-pin side is less than or smaller than this circular area of pin (116) on the single pin side. In some versions of skull clamp (10), this circular area of pins (206) on the 2-pin side is less than or equal to 0.6 times smaller than this circular area of pin (116) on the single pin side. In other versions of skull clamp (10) the magnitude of the difference in cross sectional circular areas of pins (206) compared with pin (116) can be greater or less than the example above having 0.6 times smaller circular area. In some versions of skull clamp (10), this circular area of pins (206) on the 2-pin side is about half of this circular area of pin (116) on the single pin side.

In some versions of skull clamp (10), pins (206) on the 2-pin side are different in shape compared with pin (116) on the single pin side; thus the pins (116, 206) are not uniform in this respect. In view of the teachings herein, other ways to characterize pins (116, 206), pin angles, contact areas, etc. will be apparent to those of ordinary skill in the art. Accordingly, the examples above should be considered non-exhaustive and non-limiting.

Figure 9:
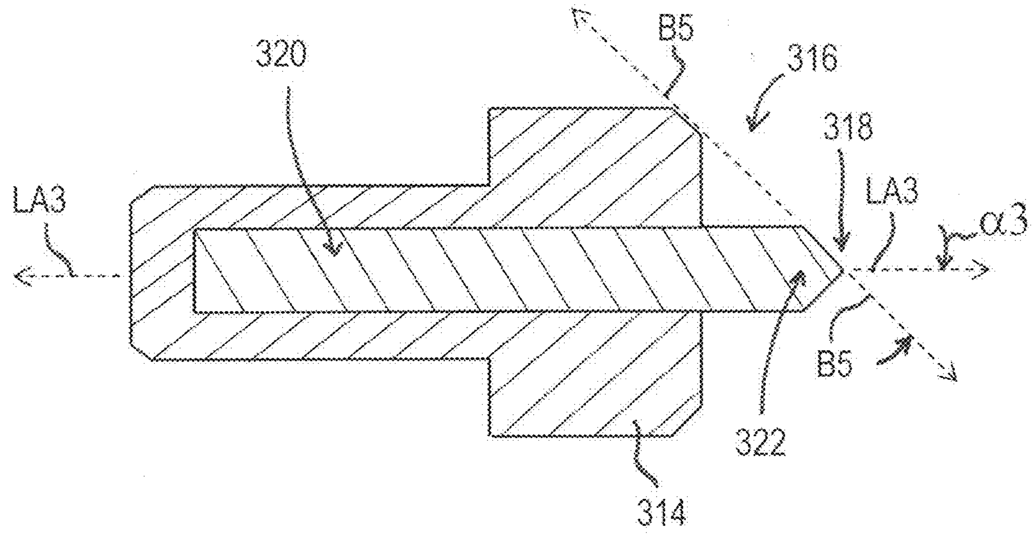
FIG. 9 depicts another exemplary pin usable with the HFD of FIG. 1.
Figure 10:
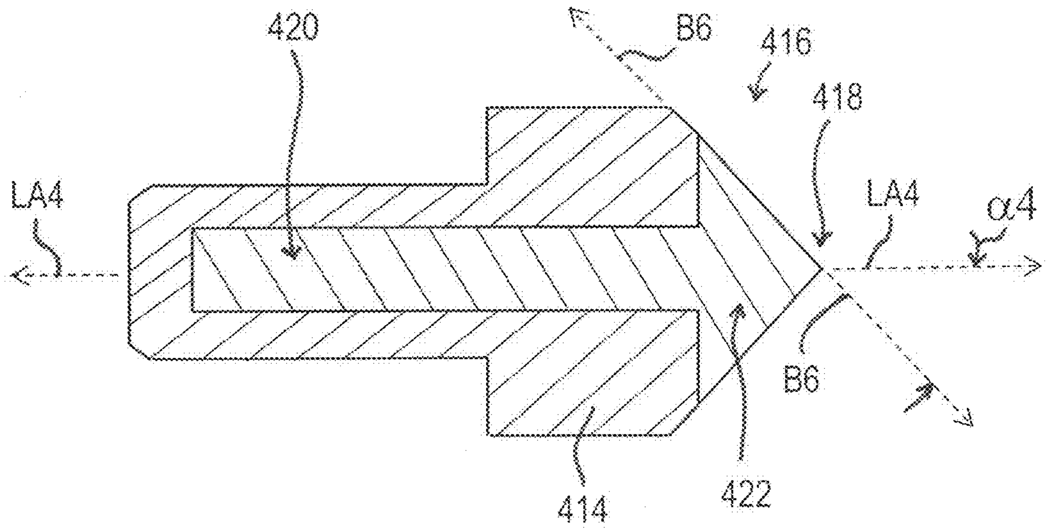
FIG. 10 depicts another exemplary pin usable with the HFD of FIG. 1.

Referring now to FIGS. 9 and 10, alternate exemplary pins (316, 416) are shown that can be used in place of any of the pins of skull clamp (10) and pin assemblies (100, 200). In one example, pin (316) or pin (416) is used instead of pin (116). Furthermore, pins (316, 416) illustrate examples having larger pin angles (α3, α4). In the present examples of FIGS. 9 and 10, pin angles (α3, α4) are about 45 degrees; however, in other versions pin angles can be more or less than about 45 degrees.

Pin angles (α3, α4) are defined in the same manner as described above with respect to pin angles (α1, α2). More specifically, pin (316) is shown in cross section in FIG. 9, and defines a longitudinal axis LA3 extending through pin (316). Furthermore, pin (316) comprises a body portion (320) and a tapered portion (322). Pin (316) further defines an axis B5, which extends from distal tip (318) proximally along pin (316). The intersection of longitudinal axis LA3 and axis B5 define a pin angle α3.

Similarly, pin (416) is shown in cross section in FIG. 10, and defines a longitudinal axis LA4 extending through pin (416). Furthermore, pin (416) comprises a body portion (420) and a tapered portion (422). Pin (416) further defines an axis B6, which extends from distal tip (418) proximally along pin (416). The intersection of longitudinal axis LA4 and axis B6 define a pin angle α4.

When replacing pin (116) with either pin (316) or pin (416) that have larger pin angles (α3, α4), the result can be that skull clamp (10) is configured such that in use, the pin (316, 416) of pin assembly (100) generates a pressure that equals the pressure generated by each pin (206) of pin assembly (200). For instance, one way to match pressures is to decrease the pin angle on the 2-pin side, while another way to match pressures is to increase the pin angle on the single pin side. Using pins (316, 416) in place of pin (116) takes this latter approach, whereas using pins (206) on the 2-pin side instead of using all pins configured like pin (116) takes the former approach to matching pressures. Still yet, in view of the teachings herein, those of ordinary skill in the art will appreciate other ways to modify the pins on one or both sides of the patient's head to achieve a uniform or more uniform pressure application.

Still referring to FIGS. 9 and 10, while each pin (316, 416) has a pin angle of about 45 degrees as defined above, pin (416) has a geometry with a larger conical shaped portion compared to pin (316). In terms of the contact area calculation from Equation 4 above, this translates to pin (416) having a larger radius of the cone portion and a larger height of the cone portion. This means that pin (416) can provide for greater contact surface area as pins (316, 416) penetrate the skull bone. In this manner the force applied when using pin (416) can be distributed over a larger area and thus provide a lower pressure. It should be noted here that in use the larger contact area for pin (416) provides a difference over pin (316) when the penetration of the pins (316, 416) is such that pins (316, 416) penetrate deeper than the cone shape or cone height of pin (316). In view of the teachings herein, other ways to influence contact area based on parameters like shape configuration will be apparent to those of ordinary skill in the art.

II. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. The following examples are being provided for nothing more than merely illustrative purposes. It is contemplated that the various teachings herein may be arranged and applied in numerous other ways. It is also contemplated that some variations may omit certain features referred to in the below examples.

Example 1

A device for stabilizing a head of a patient during a medical procedure, wherein the device comprises: (a) a first pin assembly having a first pin configured to engage a skull of the patient to stabilize the head of the patient, wherein the first pin comprises a first pin angle; and (b) a second pin assembly having a pair of pins configured to engage the skull of the patient to stabilize the head of the patient, wherein each pin of the pair of pins comprises a second pin angle different than the first pin angle of the first pin.

Example 2

The device of Example 1, wherein the first pin assembly and the second pin assembly are configured to be positioned on opposite sides of the head of the patient.

Example 3

The device of any one or more of Examples 1 through 2, wherein a longitudinal cross section of the first pin defines the first pin angle by an intersection of a longitudinal axis of the single pin with an axis of the single pin extending from a distal tip of the single pin proximally along the single pin; and wherein a longitudinal cross section of each pin of the pair of pins defines the second pin angle by an intersection of a longitudinal axis of each respective pin of the pair of pins with an axis of each respective pin of the pair of pins extending from a distal tip of each respective pin of the pair of pins proximally along each respective pin of the pair of pins.

Example 4

The device of any one or more of Examples 1 through 3, wherein the second pin angle is smaller than the first pin angle.

Example 5

The device of any one or more of Examples 1 through 4, wherein the first pin angle and the second pin angle are configured such that a pressure exerted on the head of the patient when stabilized is substantially equal where the first pin and the pair of pins each contact the head of the patient.

Example 6

The device of any one or more of Examples 1 through 5, wherein the first pin angle and the second pin angle are configured such that the first pin and the pair of pins each have a substantially equal bone penetration depth when stabilizing the head of the patient.

Example 7

The device of any one or more of Examples 1 through 6, wherein the device comprises a skull clamp having a first arm and a second arm that are selectively and adjustably connectable, wherein the first arm comprises a first upright portion connected with a first lateral portion, wherein the second arm comprises a second upright portion connected with a second lateral portion, wherein the first pin assembly connects with the first upright portion, and wherein the second pin assembly connects with the second upright portion.

Example 8

The device of any one or more of Examples 1 through 7, wherein the first pin angle and the second pin angle are each within the range of about 3 degrees to about 23 degrees with the difference between the first pin angle and the second pin angle is at least about 1 degree.

Example 9

The device of any one or more of Examples 1 through 8, wherein the first pin angle and the second pin angle are each within the range of about 3 degrees to about 45 degrees with the difference between the first pin angle and the second pin angle is at least about 1 degree.

Example 10

The device of any one or more of Examples 1 through 9, wherein the first pin assembly comprises a force adjustment feature configured to adjust an amount of force applied by the first pin to the head of the patient, wherein the amount of force applied by the first pin when stabilizing the head of the patient is between about 270 newtons and about 360 newtons.

Example 11

The device of any one or more of Examples 1 through 10, wherein a force applied by each pin of the pair of pins when stabilizing the head of the patient is between about 135 newtons and about 180 newtons.

Example 12

The device of any one or more of Examples 1 through 11, wherein the second pin angle of each pin of the pair of pins is greater than or equal to about 1 degree smaller than the first pin angle of the first pin.

Example 13

The device of any one or more of Examples 1 through 11, wherein the second pin angle of each pin of the pair of pins is between about 1 degree and about 5 degrees smaller than the first pin angle of the first pin.

Example 14

A device for stabilizing a head of a patient during a medical procedure, wherein the device comprises two or more pin assemblies, wherein each of the pin assemblies comprises at least one pin configured to engage a skull of the patient to stabilize the head of the patient, wherein the at least one pin of a select one of the two or more pin assemblies comprises a first pin angle, and wherein the at least one pin of another select one of the two or more pin assemblies comprises a second pin angle, wherein the first pin angle and the second pin angle differ.

Example 15

A device for stabilizing a head of a patient during a medical procedure, wherein the device comprises (a) a first pin assembly having a single pin configured to engage a skull of the patient to stabilize the head of the patient; and (b) a second pin assembly having a pair of pins configured to engage the skull of the patient to stabilize the head of the patient, wherein the pair of pins and the single pin are non-uniform.

Example 16

The device of Example 15, wherein the pair of pins are different in shape compared with single pin.

Example 17

A device for stabilizing a head of a patient during a medical procedure, wherein the device comprises (a) a first pin assembly having a single pin configured to engage a skull of the patient to stabilize the head of the patient, wherein the first pin comprises a first tapered portion having a first conical shape with a first radius; and (b) a second pin assembly having a pair of pins configured to engage the skull of the patient to stabilize the head of the patient, wherein the pair of pins each comprise a second tapered portion having a second conical shape with a second radius, wherein the second radius is smaller than the first radius.

Example 18

The device of Example 17, wherein the contact area of each pin of the pair of pins is less than the contact area of the single pin when the device is used to stabilize the head of the patient.

Example 19

The device of any one or more of Examples 17 through 18, wherein the single pin comprises a first circular area in cross section at a first penetration depth, and wherein each pin of the pair of pins comprises a second circular area in cross section at the first penetration depth.

Example 20

The device Example 19, wherein the second circular area is smaller than the first circular area.

III. Miscellaneous

It should be understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art.

For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A skull clamp for stabilizing a head of a patient during a medical procedure, wherein the skull clamp comprises: (a) a first arm, wherein the first arm comprises a first upright portion connected with a first lateral portion; (b) a second arm, wherein the second arm comprises a second upright portion connected with a second lateral portion; (c) at least two pin assemblies connectable with the first or second arm; and (d) a plurality of pins configured to engage a skull of the patient to stabilize the head of the patient, wherein each of the pin assemblies has at least one pin of the plurality of pins, wherein a first number of pins configured to be on a first side of the patient's head is more or less than a second number of pins configured to be on a second side of the patient's head that is opposite to the first side of the patient's head; wherein a first pin of the plurality of pins configured to be located on the first side of the patient's head comprises a first pin angle, and wherein a second pin and a third pin of the plurality of pins configured to be located on the second side of the patient's head each comprise a second pin angle, wherein the first pin angle and the second pin angle are defined by an intersection of a longitudinal axis of the respective pins with an axis of the respective pins extending from a distal tip of the respective pins proximally along a distal tapered region of the respective pins, wherein the second pin angle is smaller than the first pin angle, and wherein the first pin angle and the second pin angle are each within a range of 10 degrees to 30 degrees with a difference between the first pin angle and the second pin angle is at least 1 degree.

2. The skull clamp of claim 1, wherein the first pin angle is 25 degrees and the second pin angle is 15 degrees.

3. The skull clamp of claim 1, wherein the difference between the first pin angle and the second pin angle is up to 5 degrees.

4. The skull clamp of claim 1, wherein the second pin angle is half of the first pin angle.

5. The skull clamp of claim 1, wherein the axis of the respective pins extending from the distal tip of the respective pins proximally along the distal tapered region of the respective pins contacts the respective pins tangentially.

6. A skull clamp for stabilizing a head of a patient during a medical procedure, wherein the skull clamp comprises:

(a) a U-shape having a first upright portion positionable on a first side of the patient's head, and a second upright portion positionable on a second side of the patient's head that is opposite to the first side of the patient's head;

(b) a first pin assembly connectable with the first upright portion;

(c) a second pin assembly connectable with the second upright portion; and (d) a plurality of pins configured to engage a skull of the patient to stabilize the head of the patient, wherein each of the pin assemblies has at least one pin of the plurality of pins, wherein a first number of pins configured to be on the first side of the patient's head is more or less than a second number of pins configured to be on the second side of the patient's head, wherein a first pin of the plurality of pins configured to be located on the first side of the patient's head comprises a first pin angle, and wherein a second pin and a third pin of the plurality of pins configured to be located on the second side of the patient's head each comprise a second pin angle, wherein the first pin angle and the second pin angle are defined by an intersection of a longitudinal axis of the respective pins with an axis of the respective pins extending from a distal tip of the respective pins proximally along a distal tapered region of the respective pins, wherein the second pin angle is smaller than the first pin angle.

7. The skull clamp of claim 6, wherein the first pin angle and the second pin angle are each within the range of 10 degrees to 30 degrees with the difference between the first pin angle and the second pin angle is at least 1 degree.

8. The skull clamp of claim 6, wherein the first pin angle is 25 degrees and the second pin angle is 15 degrees.

9. The skull clamp of claim 6, wherein the difference between the first pin angle and the second pin angle is up to 5 degrees.

10. The skull clamp of claim 6, wherein the second pin angle is half of the first pin angle.

11. A skull clamp for stabilizing a head of a patient during a medical procedure, wherein the skull clamp comprises: (a) a first arm, wherein the first arm comprises a first upright portion connected with a first lateral portion; (b) a second arm, wherein the second arm comprises a second upright portion connected with a second lateral portion; (c) at least two pin assemblies connectable with the first or second arm; and (d) a plurality of pins configured to engage a skull of the patient to stabilize the head of the patient, wherein each of the pin assemblies has at least one pin of the plurality of pins, wherein a first number of pins configured to be on a first side of the patient's head is more or less than a second number of pins configured to be on a second side of the patient's head that is opposite to the first side of the patient's head; wherein a first pin of the plurality of pins configured to be located on the first side of the patient's head comprises a first circular area in cross section at a first penetration depth, and wherein each of the second and third pins comprise a second circular area in cross section at the first penetration depth, wherein the second circular area is smaller than the first circular area.

12. A method of using a skull clamp to stabilize a head of a patient comprising:

(a) engaging a first pin located on a first side of the patient's head with the head of the patient, wherein the first pin comprises a first pin angle; and (b) engaging a second pin and a third pin on a second side of the patient's head with the head of the patient, wherein the second side of the patient's head is opposite to the first side of the patient's head, wherein the second pin and the third pin each comprise a second pin angle, wherein the first pin angle and the second pin angle are defined by an intersection of a longitudinal axis of the respective pins with an axis of the respective pins extending from a distal tip of the respective pins proximally along a portion of the respective pins, wherein the second pin angle is smaller than the first pin angle.

* * * * *